United States Patent [19]
Jeppesen et al.

[11] Patent Number: 5,914,338
[45] Date of Patent: Jun. 22, 1999

[54] HETEROCYCLIC COMPOUNDS AND THEIR PREPARATION AND USE

[75] Inventors: Lone Jeppesen, Virum; Preben H. Olesen, Copenhagen NV; Per Sauerberg, Farum, all of Denmark

[73] Assignee: Novo Nordisk, Bagsvaerd, Denmark

[21] Appl. No.: 08/831,358

[22] Filed: Apr. 1, 1997

[30] Foreign Application Priority Data

Apr. 2, 1996 [DK] Denmark ................................. 0377/96
Nov. 14, 1996 [DK] Denmark ................................. 1281/96

[51] Int. Cl.⁶ ...................... A61K 31/41; C07D 285/10; C07D 417/04
[52] U.S. Cl. .......................... 514/362; 514/256; 514/339; 544/333; 546/268.7; 548/134; 548/135
[58] Field of Search ................. 548/135.134; 546/268.7; 544/333; 514/362, 339, 356

[56] References Cited

FOREIGN PATENT DOCUMENTS

| 0 307 142 | 3/1989 | European Pat. Off. . |
| 0 363 085 | 4/1990 | European Pat. Off. . |
| 0 709 381 | 5/1996 | European Pat. Off. . |
| WO 92/03433 | 3/1992 | WIPO . |
| WO 92/11261 | 7/1992 | WIPO . |
| WO 94/20496 | 9/1994 | WIPO . |

*Primary Examiner*—Richard L. Raymond
*Assistant Examiner*—Brenda Coleman
*Attorney, Agent, or Firm*—Steve T. Zelson; Elias J. Lambiris; Carol E. Rozek

[57] ABSTRACT

The present invention relates to therapeutically active aza-tricyclic compounds of formula I

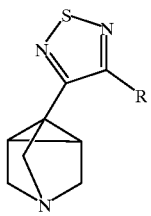

(I)

a method of preparing the same and to pharmaceutical compositions comprising the compounds. The novel compounds are useful in treating a disease in the central nervous system caused by malfunctioning of the muscarinic cholinergic system.

15 Claims, No Drawings

HETEROCYCLIC COMPOUNDS AND THEIR PREPARATION AND USE

CROSS-REFERENCE TO RELATED APPLICATIONS

This application claims priority under 35 U.S.C. 119 of Danish application no. 0377/96 filed Apr. 2, 1996 and no. 1281/96 filed Nov. 14, 1996, the contents of which are fully incorporated herein by reference.

1. Field of the Invention

The present invention relates to therapeutically active azatricyclic compounds, a method of preparing the same and to pharmaceutical or veterinary compositions comprising the compounds. The novel compounds are useful in treating a disease in the central nervous system caused by malfunctioning of the muscarinic cholinergic system.

2. Background of the Invention

Due to the generally improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic receptors in the forebrain and hippocampus still exist. Therefore cholinergic agonists are useful in the treatment of Alzheimer's disease, in halting progression of Alzheimer's disease, and in improving the cognitive functions of elderly people.

The compounds of this invention are also useful analgesic agents and therefore useful in the treatment of severe painful conditions.

Furthermore, the compounds of this invention are useful in the treatment of glaucoma, psychosis, mania, bipolar disorder, schizophrenia or schizophreniform conditions, depression, bladder dysfunctions, anxiety, sleeping disorders, epilepsy, cerebral ischemia and gastrointestinal motility disorders.

SUMMARY OF THE INVENTION

It is an object of the invention to provide new muscarinic cholinergic compounds.

The novel compounds of the invention are heterocyclic compounds of formula I

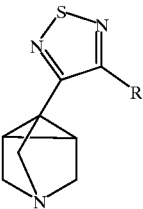

(I)

wherein
R is hydrogen, halogen, $—NR^1R^2$, $—R^3$, $—OR^3$, $—SR^3$, $—SOR^3$, $—SO_2R^3$, $C_{3-8}$-cycloalkyl, $C_{4-12}$-(cycloalkylalkyl), $—Z-C_{3-10}$-cycloalkyl and $—Z-C_{4-12}$-(cycloalkylalkyl) wherein $R^3$ is hydrogen, straight or branched $C_{1-15}$-alkyl, straight or branched $C_{2-15}$-alkenyl, straight or branched $C_{2-15}$-alkynyl or straight or branched $C_{4-15}$-alkenynyl, each of which is optionally substituted with one or more selected from halogen(s), $—CF_3$, $—CN$, $—OH$, Y, phenyl or phenoxy wherein phenyl or phenoxy is optionally substituted with one or more selected from halogen(s), $—OH$, $—CF_3$, $—CN$, $C_{1-4}$-alkyl, $C_{1-4}$-alkoxy, $C_{1-4}$-alkylthio, $—SCF_3$, $—OCF_3$, $—CONH_2$ or $—CSNH_2$; or
R is phenyl or benzyloxycarbonyl, each of which is optionally substituted with one or more selected from halogen(s), $—OH$, $—CF_3$, $—CN$, $C_{1-4}$-alkyl, $C_{1-4}$-alkoxy, $C_{1-4}$-alkylthio, $—SCF_3$, $—OCF_3$, $—CONH_2$ or $—CSNH_2$; or
R is $—OR^4ZY$, $—SR^4ZY$, $—OR^4ZR^3$ or $—SR^4ZR^3$ wherein Z is oxygen or sulphur, $R^4$ is straight or branched $C_{1-15}$-alkylene, straight or branched $C_{2-15}$-alkenylene, straight or branched $C_{2-15}$-alkynylene or straight or branched $C_{4-15}$-alkenynylene, each of which is optionally substituted with one or more selected from halogen(s), $—CF_3$, $—CN$, $—OH$, Y, phenyl or phenoxy wherein phenyl or phenoxy is optionally substituted with one or more selected from halogen(s), $—OH$, $—CF_3$, $—CN$, $C_{1-4}$-alkyl, $C_{1-4}$-alkoxy, $C_{1-4}$-alkylthio, $—SCF_3$, $—OCF_3$, $—CONH_2$ or $—CSNH_2$;
Y is a 5 or 6 membered heterocyclic group, which heterocyclic group is optionally substituted at carbon or nitrogen atom(s) with one or more selected from halogen(s), $—OH$, $—CF_3$, $—CN$, $C_{1-4}$-alkyl, $C_{1-4}$-alkoxy, $C_{1-4}$-alkylthio, $—SCF_3$, $—OCF_3$, $—CONH_2$, $—CSNH_2$, phenyl, benzyl or thienyl, or a carbon atom in the heterocyclic group together with an oxygen atom form a carbonyl group, or which heterocyclic group is optionally fused with a phenyl group;
$R^1$ and $R^2$ independently are hydrogen or $C_{1-6}$-alkyl, or $R^1$ and $R^2$ together with the nitrogen atom optionally form a 4- to 6-membered ring; or a pharmaceutically acceptable salt or solvate thereof.

As used herein, the term "halogen" means F, Cl, Br, and I. Especially preferred halogens include Cl, Br, and F.

The term "$C_{1-n'}$-alkyl" wherein n' can be from 2 through 15, as used herein, represents a branched or straight alkyl group having from one to the specified number of carbon atoms. Typical $C_{1-6}$-alkyl groups include, but are not limited to, methyl, ethyl, n-propyl, iso-propyl, butyl, iso-butyl, sec-butyl, tert-butyl, pentyl, hexyl and the like.

The term "$C_{2-n'}$-alkenyl" wherein n' can be from 3 through 15, as used herein, represents an olefinically unsaturated branched or straight group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_{2-n'}$-alkynyl" wherein n' can be from 3 through 15, as used herein, represents an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The term "$C_{4-n'}$-alkenynyl" wherein n' can be from 5 through 15, as used herein, represents an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like.

The term "$C_{3-n'}$-cycloalkyl" wherein n' can be from 4 through 10, as used herein, represents e.g. cyclopropyl, cyclobutyl, cyclopentyl, cyclohexyl, cycloheptyl and cyclooctyl and the like.

As used herein the term "$C_{4-12}$-(cycloalkylalkyl)" represents a branched or straight alkyl group substituted at a carbon with a cycloalkyl group. Examples of such groups include, but are not limited to, cyclopropylethyl, cyclobutylmethyl, 2-(cyclohexyl)ethyl, cyclohexylmethyl, 3-(cyclopentyl)-1-propyl, and the like.

The term "$C_{1-4}$-alkoxy" as used herein, alone or in combination, refers to a straight or branched monovalent substituent comprising a $C_{1-4}$-alkyl group linked through an ether oxygen having its free valence bond from the ether oxygen and having 1 to 4 carbon atoms. Examples of such groups include, but are not limited to, e.g. methoxy, ethoxy, propoxy, isopropoxy, butoxy and the like.

The term "$C_{1-4}$-alkylthio" as used herein, alone or in combination, refers to a straight or branched monovalent substituent comprising a $C_{1-4}$-alkyl group linked through a divalent sulfur atom having its free valence bond from the sulfur oxygen and having 1 to 4 carbon atoms. Examples of such groups include, but are not limited to, e.g. methylthio, ethylthio, propylthio, isopropylthio, butylthio and the like.

As used herein, the phrase "$R^1$ and $R^2$ together with the nitrogen atom optionally form a 4- to 6-membered ring" for example, includes, but is not limited to:

As used herein, the phrase "5 or 6 membered heterocyclic group" means a group containing from one to four N, O or S atom(s) or a combination thereof, which heterocyclic group is optionally substituted at carbon or nitrogen atom(s) with halogen, —OH, —$CF_3$, —CN, $C_{1-4}$-alkyl, $C_{1-4}$-alkoxy, $C_{1-4}$-alkylthio, —$SCF_3$, —$OCF_3$, —$CONH_2$, —$CSNH_2$, phenyl, benzyl or thienyl, or a carbon atom in the heterocyclic group together with an oxygen atom form a carbonyl group, or which heterocyclic group is optionally fused with a phenyl group. The phrase "5 or 6 membered heterocyclic group" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having four heteroatoms; 6-membered heterocycles with one heteroatom (e.g. pyridine, quinoline, isoquinoline, phenanthridine, cyclohepta[b]pyridine); 6-membered heterocycles with two heteroatoms (e.g. pyridazines, cinnolines, phthalazines, pyrazines, pyrimidines, quinazolines); 6-membered heterocycles with three heteroatoms (e.g. 1,3,5-triazine); and 6-membered heterocycles with four heteroatoms.

As used herein the term "carboxy" refers to a substituent having the common meaning understood by the skilled artisan, wherein the point of attachment may be through the carbon or oxygen atom of the group.

As used herein, the phrase "one or more selected from" shall more preferably refer to from 1–3 substituents. The term shall further preferably refer to from 1–2 substituents.

In a preferred embodiment, the present invention is concerned with compounds of formula I wherein R is —$OR^3$, —$SR^3$, —$OR^4ZY$, —$SR^4ZY$, —$OR^4ZR^3$ or —$SR^4ZR^3$, wherein $R^3$, $R^4$, Y and Z are as defined above.

In another preferred embodiment, the present invention is concerned with compounds of formula I wherein R is —$OR^3$ or —$SR^3$, wherein $R^3$ is as defined above.

In another preferred embodiment, the present invention is concerned with compounds of formula I wherein R is —$OR^4ZY$, —$SR^4ZY$, —$OR^4ZR^3$ or —$SR^4ZR^3$, wherein $R^3$, $R^4$, Y and Z are as defined above.

In another preferred embodiment, the present invention is concerned with compounds of formula I wherein R is —$OR^3$ or —$SR^3$, wherein $R^3$ is straight or branched $C_{1-5}$-alkyl, straight or branched $C_{2-15}$-alkenyl, straight or branched $C_{2-15}$-alkynyl or straight or branched $C_{4-15}$-alkenynyl, each of which is optionally substituted with one or more halogen (s), —$CF_3$, —CN, —OH, Y or phenyl wherein phenyl is optionally substituted with one or more selected from halogen(s), —OH, —$CF_3$, —CN, $C_{1-4}$-alkyl, $C_{1-4}$-alkoxy, $C_{1-4}$-alkylthio, —$SCF_3$, —$OCF_3$, —$CONH_2$ or —$CSNH_2$, and wherein Y is a 5 or 6 membered heterocyclic group, which heterocyclic group is optionally substituted at carbon or nitrogen atom(s) with one or more selected from halogen (s), —$CF_3$, —CN, $C_{1-4}$-alkyl, $C_{1-4}$-alkoxy, $C_{1-4}$-alkylthio, —$SCF_3$, or —$OCF_3$.

In another preferred embodiment, the present invention is concerned with compounds of formula I wherein R is —$OR^4ZY$, —$SR^4ZY$, —$OR^4ZR^3$ or —$SR^4ZR^3$, wherein Z is oxygen or sulphur, $R^3$ is straight or branched $C_{1-15}$-alkyl, straight or branched $C_{2-15}$-alkenyl, straight or branched $C_{2-15}$-alkynyl or straight or branched $C_{4-15}$-alkenynyl, $R^4$ is straight or branched $C_{1-15}$-alkylene, straight or branched $C_{2-15}$-alkenylene, straight or branched $C_{2-15}$-alkynylene or straight or branched $C_{4-15}$-alkenynylene, wherein $R^3$ and $R^4$ independently are optionally substituted with one or more halogen(s), —$CF_3$, —CN, —OH, Y or phenyl wherein phenyl is optionally substituted with one or more selected from halogen(s), —OH, —$CF_3$, —CN, $C_{1-4}$-alkyl, $C_{1-4}$-alkoxy, $C_{1-4}$-alkylthio, —$SCF_3$, —$OCF_3$, —$CONH_2$ or —$CSNH_2$, and wherein Y is a 5 or 6 membered heterocyclic group, which heterocyclic group is optionally substituted at carbon or nitrogen atom(s) with one or more selected from halogen(s), —$CF_3$, —CN, $C_{1-4}$-alkyl, $C_{1-4}$-alkoxy, $C_{1-4}$-alkylthio, —$SCF_3$, or —$OCF_3$.

In another preferred embodiment, the present invention is concerned with compounds of formula I wherein R is —$OR^3$ or —$SR^3$, wherein $R^3$ is $C_{2-8}$-alkynyl, preferably propynyl, substituted with phenyl or Y, preferably Y is thiophene, furan, pyrrole, oxazole, thiazole, imidazole, oxadiazole or thiadiazole, particularly preferred is thiophene, pyridine, pyrimidine or furan, each of which is optionally substituted with one or more selected from —OH, halogen(s), —$NO_2$, —CN, $C_{1-4}$-alkyl, $C_{1-4}$-alkylthio, $C_{1-4}$-alkoxy, —$SCF_3$, —OCF$_3$, —CF$_3$, —CONH$_2$ and —CSNH$_2$, preferably halogen, —CN, C$_{1-4}$-alkoxy or —OCF$_3$.

It is to be understood that the invention extends to each of any of the stereoisomeric forms of the compounds of the present invention as well as the pure diastereomeric, pure enantiomeric, and racemic forms of the compounds of this invention.

The starting materials for the illustrated process are, if nothing else mentioned, commercially available or may be prepared using methods known to the skilled artisan.

The invention also relates to methods of preparing the above mentioned compounds, comprising:

a) reduction with DIBAL-H in toluene of a tricyclic nitrile of formula II (described in WO 92/11261)

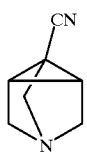
(II)

to an aldehyde of formula III

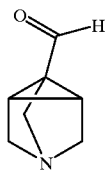
(III)

which is converted to the corresponding aminonitrile of formula IV

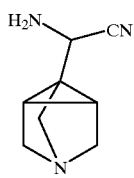
(IV)

under conventional conditions such as adding the aldehyde of formula III to a solution of potassium cyanide and ammonium chloride (Strecker condition) or stepwise by reacting the aldehyde with potassium cyanide forming the cyanohydrin which after isolation can be reacted with ammonium chloride under basic aqueous conditions to give the aminonitrile, and subsequently cyclization of the aminonitrile with sulfur monochloride in an aprotic solvent such as dimethyl formamide to form a compound of formula I wherein R is halogen; or b) reacting a compound of formula V prepared as described under a)

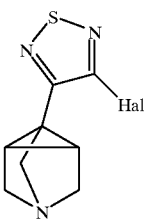
(V)

wherein Hal is halogen, with sodium hydrosulfide in an aprotic solvent such as dimethyl formamid followed by the appropriate alkylhalide to form a compound of formula I wherein R is —SR$^3$, —S-C$_{3-10}$-cycloalkyl, —S-C$_{4-12}$-cycloalkyl, —SR$^4$ZY or —SR$^4$ZR$^3$ wherein R$^3$, R$^4$, Y and Z are defined as above; or c) oxidating a compound of formula I wherein R is —SR$^3$, wherein R$^3$ is defined as above to form a compound of formula I wherein R is —SOR$^3$ or —SO$_2$R$^3$ wherein R$^3$ is as defined above. Oxone is an especially preferred oxidazing agent for this process; or d) reacting a sulfone of formula VI, prepared as described under c)

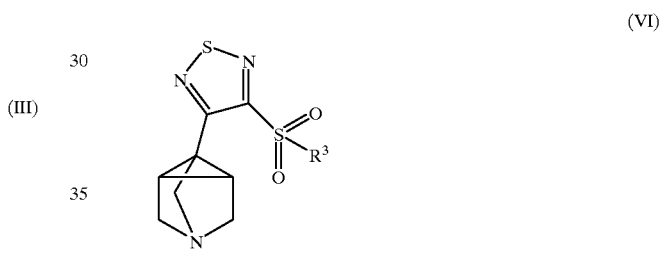
(VI)

wherein R$^3$ is as defined above, with sodium hydrosulfide in an aprotic solvent such as dimethyl formamide followed by the appropriate alkylhalide to obtain a compound of formula I wherein R is —S—R$^3$, —S-C$_{3-10}$-cycloalkyl, —S-C$_{4-12}$-cycloalkylalkyl, —SR$^4$ZY, —SR$^4$ZR$^3$ wherein R$^3$, R$^4$, Y and Z are defined as above; or e) reacting a sulfone of formula VI prepared as described above

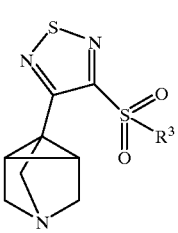
(VI)

wherein R$^3$ is as defined above with an appropriate alcohol and a base in example sodium hydride to obtain a compound of formula I wherein R is —OR$^3$, —O-C$_{3-10}$-cycloalkyl, —O-C$_{4-12}$-cycloalkylalkyl, —OR$^4$ZY, —OR$^4$ZR$^3$ wherein R$^3$, R$^4$, Y and Z are defined as above; or f) reacting a compound of formula V prepared as described under a)

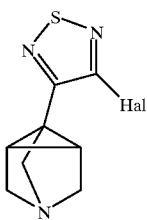

(V)

wherein Hal is halogen, with an appropriate alcohol and a base in example sodium hydride to obtain a compound of formula I wherein R is —OR$^3$, —O—C$_{3-10}$-cycloalkyl, —O-C$_{4-12}$-cycloalkylalkyl, —OR$^4$ZY, —OR$^4$ZR$^3$ where R$^3$, R$^4$, Y and Z are defined as above; or g) reacting a compound of formula V prepared as described under a)

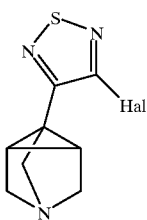

(V)

wherein Hal is halogen, with an appropriate amine to obtain a compound of formula I wherein R is —NR$^1$R$^2$, wherein R$^1$ and R$^2$ are as defined above; or h) reducing a compound of formula V prepared as described under a)

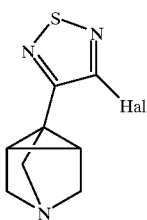

(V)

wherein Hal is halogen, to obtain a compound of formula I wherein R is hydrogen; or i) reacting a compound of formula V prepared as described under a)

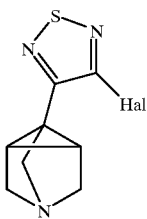

(V)

wherein Hal is halogen, with an appropriate Grignard reagent in a solvent as tetrahydrofuran to obtain a compound of formula I wherein R is R$^3$, C$_{3-8}$-cycloalkyl, C$_{4-12}$-cycloalkylalkyl, phenyl or benzyloxycarbonyl; or j) reacting a compound of formula V prepared as described under a)

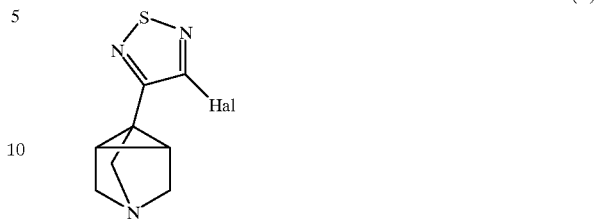

wherein Hal is halogen, with sodium hydrogensulfide to obtain a compound of formula I wherein R i —SH; or k) reacting a compound of formula VII prepared as described above

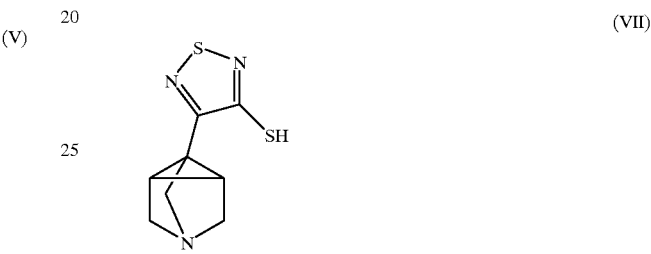

with an appropriate alcohol in the presence of a phosphorus (III) compound, e.g., triphenylphosphine, and a diester of azodicarboxylate, e.g. diethyl azodicarboxylate to give a compound of formula I wherein R is SR$^3$, SR$^4$ZY or SR$^4$ZR$^3$ wherein R$^3$, R$^4$, Z and Y are defined as above.

As is always the case in chemistry, the rate of the reaction depends on a variety of factors, such as the temperature and the exact compound which is to be prepared. The course of the reaction may be followed using methods such as thin layer chromatography (TLC), high performance liquid chromatography (HPLC), gas chromatography (GC) and nuclear magnetic resonance spectroscopy (NMR) to detect the degree of completion of the reaction. The operator may obtain maximum yields using the process by extending the reaction time. Alternatively, the operator may wish to obtain maximum throughput by cutting off the reaction at the point at which it reaches an economical degree of completion.

When the product of a step in the following process is an oil, it may be isolated by standard methods. Such methods include distillation, flash chromatography, HPLC and the like.

The invention further provides a formulation comprising a compound of formula I and one or more pharmaceutically acceptable diluents, carriers or excipients therefor. Such compositions are preferably in the form of an oral dosage unit or parenteral dosage unit.

The invention provides a method for treating a condition associated with a malfunction of the cholinergic muscarinic receptor system comprising administering to a subject in need thereof a pharmaceutically effective amount of a compound according to the invention. Such conditions which may be treated using a compound of this invention include, but are not limited to Alzheimer's Disease, cognitive dysfunction, severely painful conditions, glaucoma, psychosis, schizophrenia, bladder dysfunction, anxiety, sleep disorders, and other such conditions associated with the modulation of a muscarinic receptor.

As used herein the term "treating" includes prophylaxis of a physical and/or mental condition or amelioration or elimination of the developed physical and/or mental condition once it has been established or alleviation of the characteristic symptoms of such condition.

As used herein the term "malfunctioning of the muscarinic cholinergic system" shall have the meaning accepted by the skilled artisan. For example the term shall refer to, but is not in any way limited to conditions such as glaucoma, psychosis, schizophrenia or schizophreniform conditions, depression, sleeping disorders, epilepsy and gastrointestinal motility disorders. Other such conditions include Alzheimer's disease and incontinence.

As used herein the phrase "interacting with a muscarinic cholinergic receptor" shall include compounds which block muscarinic cholinergic receptors or modulate such receptors. The phrase shall include the effect observed when compounds act as agonists, partial agonists and/or antagonists at a muscarinic cholinergic receptor.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-Oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer is rinsed with 10 ml of buffer and the combined suspension centrifuged for 15 min. at 40,000×g. The pellet is washed three times with buffer. In each step the pellet is homogenized as before in 2×10 ml of buffer and centrifuged for 10 min. at 40,000×g.

The final pellet is homogenized in 20 mM Hepes pH: 7.4 (100 ml per g of original tissue) and used for binding assay. Aliquots of 0.5 ml is added 25 μl of test solution and 25 μl of $^3$H-Oxotremorine (1.0 nM, final concentration) mixed and incubated for 30 min. at 25° C. Non-specific is determined in triplicate using arecoline (1 μg/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steambath for less than 5 min.) at a concentration of 2.2 mg/ml. 25–75% inhibition of specific binding must be obtained before calculation of $IC_{50}$.

The test value will be given as $IC_{50}$ (the concentration (nM) of the test substance which inhibits the specific binding of $^3$H-Oxo by 50%).

$$IC_{50} = \text{(applied test substance concentration)} \times (C_x/C_o - C_x) nM$$

where $C_o$ is specific binding in control assays and $C_x$ is the specific binding in the test assay. (The calculations assume normal mass-action kinetics).

Furthermore, the pharmacological properties of the compounds of the invention can also be illustrated by determining their capability to inhibit $^3$H-PRZ (pirenzepine, [N-methyl-$^3$H]) binding to rat cerebral cortex membranes. Pirenzepine binds selectively to subtype of muscarinic receptors. Historically the type is named the $M_1$-site, whereas pirenzepine sensitive site would be more appropriate. Although selective for $M_1$-sites pirenzepine also interact with $M_2$-sites.

All preparations are performed at 0–4° C. unless otherwise indicated. Fresh cortex (0.1–1 g) from male Wistar rats (150–200 g) is homogenized for 5–10 s. in 10 ml 20 mM Hepes pH: 7.4, with an Ultra-Turrax homogenizer. The homogenizer is rinsed with 2×10 ml of buffer and the combined suspension centrifuged for 15 min at 40,000×g. The pellet is washed three times with buffer. In each step the pellet is homogenized as before in 3×10 ml of buffer and centrifuged for 10 min at 40,000×g.

The final pellet is homogenized in 20 mM Hepes pH: 7.4 (100 ml per g of original tissue) and used for binding assay. Aliquots of 0.5 ml is added 20 μl of test solution and 25 μl of $^3$H-Pirenzepine (1.0 nM, final conc.), mixed and incubated for 60 min at 20° C. Non-specific binding is determined in triplicate using atropine (1 μg/ml, final conc.) as the test substance. After incubation samples are added 5 ml of ice-cold buffer and poured directly onto Whatman GF/C glass fibre filters under suction and immediately washed 2 times with 5 ml of ice-cold buffer. The amount of radioactivity on the filters are determined by conventional liquid scintillation counting. Specific binding is total binding minus non-specific binding.

Test substances are dissolved in 10 ml water, at a concentration of 0.22 mg/ml. 25–75% inhibition of specific binding must be obtained before calculation of $IC_{50}$.

The test value will be given as $IC_{50}$ (the concentration (nM) of the test substance which inhibits the specific binding of $^3$H-PRZ by 50%).

$$IC_{50} = \text{(applied test substance concentration)} \times (C_x/C_o - C_x) nM$$

where $C_o$ is specific binding in control assays and $C_x$ is the specific binding in the test assay. (The calculations assume normal mass-action kinetics).

Test results obtained by testing some compounds of the present invention will appear from the following table 1:

TABLE 1

| Compound | $^3$H-Oxo $IC_{50}$, nM | $^3$H-PRZ $IC_{50}$, nM |
|---|---|---|
| 2 | 4.3 | 100 |
| 3 | 14.0 | 245 |
| 4 | 41.0 | 500 |

TABLE 1-continued

| Compound | $^3$H-Oxo $IC_{50}$, nM | $^3$H-PRZ $IC_{50}$, nM |
|---|---|---|
| 6 | 17.0 | 93 |
| 7 | 26.0 | 183 |
| 8 | 8.7 | 180 |
| 9 | 15.0 | 284 |
| 10 | 25.0 | 326 |
| 11 | 6.0 | 400 |

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients suffering from diseases in the central nervous system caused by malfunctioning of the muscarinic cholinergic system it may frequently be necessary to begin with a dosage of from about 20 to about 70 mg per day and when the condition is under control to reduce the dosage as low as from about 0.1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, depot, subcutaneous, intravenous, intraurethral, intramuscular, intranasal, ophthalmic solution or an ointment, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

A typical tablet, appropriate for use in this method, may be prepared by conventional tabletting techniques and contains:

| Active compound | 5.0 | mg |
|---|---|---|
| Lactosum | 67.8 | mg Ph. Eur. |
| Avicel ® | 31.4 | mg |
| Amberlite ® | 1.0 | mg |
| Magnesii stearas | 0.25 | mg Ph. Eur. |

The compounds according to this invention may be suitable for administration to an animal. Such animals include both domestic animals, for example livestock, laboratory animals, and household pets, and non-domestic animals such as wildlife. More preferably, the animal is a vertebrate. Most preferably, a compound according to this invention shall be administered to a mammal. It is especially preferred that the animal is a domestic mammal or a human. The most preferred mammal is a human. For such purposes, a compound of this invention may be administered as a feed additive or in bulk form.

The invention will now be described in further detail with reference to the following examples. The examples are provided for illustrative purposes, and are not to be construed as limiting the scope of the invention in any way.

EXAMPLE 1

A. 1-Formyl-4-azatricyclo[2.2.1.0$^{2,6}$]heptane

1-Cyano-4-azatricyclo[2.2.1.0$^{2,6}$]heptane (WO92/11261) (5.0 g, 42 mmol) in dry THF (150 ml) was treated with diisobutylaluminium hydride (84 ml of a 1M solution in hexane, 84 mmol) at 0° C. under nitrogen. After 3H the reaction mixture was allowed to warm to room temperature and quenched with 4N HCl. The THF was removed by concentrating in vacuo and the residue extracted with ethyl acetate (2x-discarded). The aqueous phase was made basic (pH 10–11) with potassium carbonate and the mixture extracted with dichloromethane (6x). The dichloromethane extracts were dried (MgSO$_4$) and filtered. Evaporation of the solvent gave 2.8 g (55%) of the title compound.

B. 2-Amino-2-(4-azatricyclo[2.2.1.0$^{2,6}$]hept-1-yl) acetonitrile

To an icecooled solution of 1-formyl-4-azatricyclo [2.2.1.0$^{2,6}$]heptane (3.56 g, 29 mmol) in water (5 ml) was added a solution of potassium cyanide (2.08 g, 31.9 mmol) in water (5 ml) over 30 min. After an additional 1 h, cooling was removed and the reaction stirred at room temperature for 16 h. The cyanohydrin product was then added 25% aqueous ammonia (4.0 ml, 52 mmol) and ammonium chloride (7.76 g, 145 mmol). The reaction mixture was stirred at room temperature for 18 h and then extracted with isopropanole/dichloromethane (1:10) (10×75 ml). The organic phases were dried and evaporated to give the title compound as an oil (2.5 g, 58%).

C. 1-(3-Chloro-1,2,5-thiadiazol-4-yl)-4-azatricyclo [2.2.1.0$^{2,6}$]heptane

To a solution of sulfur monochloride (3.2 ml, 40.2 mmol) in DMF (5 ml) was over 30 min. added a solution of crude 2-amino-2-(4-azatricyclo[2.2.1.0$^{2,6}$]hept-1-yl)acetonitrile (3.0 g, 20.1 mmol) in DMF (5 ml) at 5–10° C. The reaction mixture was stirred for an additional 1 h at 5–10° C. after which ice-water (12 ml) was added to the reaction. Sulfur precipitated and the mixture was filtered. The filtrate was made basic (pH ~10) with 4N NaOH. The product was extracted with dichloromethane (4×). The organic phases were dried and evaporated and the residue purified by column chromatography on silica gel using dichloromethane graduated to dichloromethane/methanol (9:1) as eluent. The title compound was obtained as an oil in 2.1 g (48%) yield. (Compound 1).

EXAMPLE 2

1-(3-Propylthio-1,2,5-thiadiazol-4-yl)-4-azatricyclo [2.2.1.0$^{2,6}$]heptane, oxalate A solution of 1-(3-chloro-1,2,5-thiadiazol-4-yl)-4-azatricyclo[2.2.1.0$^{2,6}$]heptane (700 mg, 3.3 mmol) and sodium hydrogen sulfide, monohydrate (730 mg, 9.9 mmol) in DMF (20 ml) was stirred at room temperature under nitrogen for 1 h. 1-Propylbromide (900 μl, 9.9 mmol) and potassium carbonate (4.6 g, 33 mmol) was added, and the reaction mixture was stirred at room temperature for 30 min. 4N HCl was added (pH ~2.0) and the mixture extracted with ether (2×- discarded). The aqueous phase was made basic (pH 10–11) with 2N NaOH and the mixture extracted with ether (3×). The ether phases were dried and evaporated. Crystallization of the residue with oxalic acid from acetone gave the title compound in 935 mg (82%) yield. M.p. 151–154° C. (Compound 2).

EXAMPLE 3

The following compounds were made in exactly the same manner as described in example 2 using the appropriate alkylbromide:
1-(3,3,3-Trifluoropropylthio-1,2,5-thiadiazol-4-yl)-4-azatricyclo[2.2.1.0$^{2,6}$]heptane, oxalate. Yield: 79%. M.p. 147–150° C. (Compound 3).
1-[3-(4-Cyanobenzylthio)-1,2,5-thiadiazol-4-yl]-4-azatricyclo[2.2.1.0$^{2,6}$]heptane, oxalate. Yield:43%. M.p. 102–105° C. (Compound 4).

EXAMPLE 4

1-(3-Propylsulfonyl-1,2,5-thiadiazol-4-yl)-4-azatricyclo[2.2.1.0$^{2,6}$]heptane, oxalate 1-(3-Propylthio-1,2,5-thiadiazol-4-yl)-4-azatricyclo [2.2.1.0$^{2,6}$]heptane (Compound 2) (585 mg, 1.7 mmol) was dissolved in water (20 ml) and 1 N HCl (2 ml) and the solution cooled in ice-water. Oxone (1.57 g, 2.55 mmol) in water (10 ml) was added under stirring. Cooling was removed and the reaction stirred for 2.5 h. The reaction was made basic (pH 10–11) with 5N NaOH and then extracted with ether (6×). The organic phases were dried (MgSO$_4$) and the solvent evaporated. Crystallization of the residue with oxalic acid from acetone gave the title compound in 545 mg (83%) yield. M.p. 187–191° C. (Compound 5).

EXAMPLE 5

1-(3-[3-(4-Fluorophenyl)-2-propynyl-1-oxy]-1,2,5-thiadiazol-4-yl)-4-azatricyclo[2.2.1.0$^{2,6}$]heptane, oxalate To a solution of 3-(4-fluorophenyl)-2-propyn-1-ol (430 mg, 2.10 mmol) in dry THF (10 ml) was slowly added sodium hydride (80%) (80 mg, 2.7 mmol) under N$_2$ and stirring. After 1 h 1-(3-propylsulfonyl-1,2,5-thiadiazol-4-yl)-4-azatricyclo[2.2.1.0$^{2,6}$]heptane (Compound 5) (200 mg, 0.7 mmol) in dry THF (3 ml) was added. Stirring was continued for 5 days. The reaction was quenched by addition of 6N HCl (pH 2) and the solvent evaporated. The residue was dissolved in water and extracted with ether (3×- discarded). The aqueous phase was made basic with 4N NaOH (pH 10–11) and the mixture extracted with ether (4×). The extracts were dried and the solvent evaporated. The product was taken up in acetone and precipitated with oxalic acid in acetone to give 235 mg (80%) of the title compound. Yield: 80%. M.p. 185–187° C. (Compound 6).

EXAMPLE 6

The following compounds were made in the same manner as described in example 5 using the appropriate alcohol:
1-[3-(3-Phenyl-2-propynyl-1-oxy)-1,2,5-thiadiazol-4-yl]-4-azatricyclo[2.2.1.0$^{2,6}$]heptane, oxalate. Yield: 76%. M.p. 182–185° C. (Compound 7).
1-(3-[3-(3-Thienyl)-2-propyn-1-yloxy]-1,2,5-thiadiazol-4-yl)-4-azatricyclo[2.2.1.0$^{2,6}$]heptane, oxalate. Yield: 67%. M.p. 180–182° C. (Compound 8).
1-(3-[3-(2-Thienyl)-2-propyn-1-yloxy]-1,2,5-thiadiazol-4-yl)-4-azatricyclo[2.2.1.0$^{2,6}$]heptane, oxalate. Yield: 77%. M.p. 156–158° C. (Compound 9).
1-(3-[3-(3-Methoxyphenyl)-2-propyn-1-yloxy]-1,2,5-thiadiazol-4-yl)-4-azatricyclo[2.2.1.0$^{2,6}$]heptane, hydrochloride. Yield: 61%. M.p. 108–111° C. (Compound 10).
1-(3-[3-(3-Pyridyl)-2-propyn-1-yloxy]-1,2,5-thiadiazol-4-yl)-4-azatricyclo[2.2.1.0$^{2,6}$]heptane, oxalate. Yield: 40%. M.p. 169–172° C. (Compound 11).
1-(3-[3-(3-Furyl)-2-propyn-1-yloxy]-1,2,5-thiadiazol-4-yl)-4-azatricyclo[2.2.1.0$^{2,6}$]heptane, oxalate. Yield: 69%. M.p. 166–167° C. (Compound 12).
1-(3-[3-(4-Methoxyphenyl)-2-propyn-1-yloxy]-1,2,5-thiadiazol-4-yl)-4-azatricyclo[2.2.1.0$^{2,6}$]heptane, oxalate. Yield: 69%. M.p. 155–158° C. (Compound 13).
1-(3-[3-(2-Pyridyl)-2-propyn-1-yloxy]-1,2,5-thiadiazol-4-yl)-4-azatricyclo[2.2.1.0$^{2,6}$]heptane, oxalate. Yield: 20%. M.p. 158–160° C. (Compound 14).
1-(3-[3-(2-Thienyl)-4-methyl-1-pentyn-3-yloxy]-1,2,5-thiadiazol-4-yl)-4-azatricyclo[2.2.1.0$^{2,6}$]heptane, oxalate. Yield: 39%. M.p. 164–165° C. (Compound 15).
1-(3-[3-(4-Chlorophenyl)-2-propyn-1-yloxy]-1,2,5-thiadiazol-4-yl)-4-azatricyclo[2.2.1.0$^{2,6}$]heptane, oxalate. Yield: 60%. M.p. 172–173,5° C. (Compound 16).
1-(3-[3-(3-Chlorophenyl)-2-propyn-1-yloxy]-1,2,5-thiadiazol-4-yl)-4-azatricyclo[2.2.1.0$^{2,6}$]heptane, oxalate. Yield: 78%. M.p. 160–162° C. (Compound 17).
1-(3-[3-(3,5-Difluorophenyl)-2-propyn-1-yloxy]-1,2,5-thiadiazol-4-yl)-4-azatricyclo[2.2.1.0$^{2,6}$]heptane, oxalate. Yield: 48%. M.p. 173–175° C. (Compound 18).
1-(3-[3-(3-Trifluoromethylphenyl)-2-propyn-1-yloxy]-1,2,5-thiadiazol-4-yl)-4-azatricyclo[2.2.1.0$^{2,6}$]heptane, oxalate. Yield: 44%. M.p. 143–144° C. (Compound 19).
1-(3-[3-(5-Chloro-2-thienyl)-2-propyn-1-yloxy]-1,2,5-thiadiazol-4-yl)-4-azatricyclo[2.2.1.0$^{2,6}$]heptane, oxalate. Yield: 80%. M.p. 155–157° C. (Compound 20).
1-(3-[3-(3,5-Dichlorophenyl)-2-propyn-1-yloxy]-1,2,5-thiadiazol-4-yl)-4-azatricyclo[2.2.1.0$^{2,6}$]heptane, oxalate. Yield: 22%. M.p. 121–124° C. (Compound 21).
1-(3-[3-(Trifluoromethoxyphenyl)-2-propyn-1-yloxy]-1,2,5-thiadiazol-4-yl)-4-azatricyclo[2.2.1.0$^{2,6}$]heptane, oxalate. Yield: 58%. M.p. 121–124° C. (Compound 29).

EXAMPLE 7

1-(3-[3-Phenyl-2-propynthio]-1,2,5-thiadiazol-4-yl)-4-azatricyclo[2.2.1.0$^{2,6}$]heptane, oxalate.

A solution of 1-(3-propylsulphonyl-1,2,5-thiadiazol-4-yl)-4-azatricyclo[2.2.1.0$^{2,6}$]heptane (Compound 5) (450 mg, 1.5 mmol) in dry DMF (20 ml) was added sodium hydrogen sulfide, monohydrate (390 mg, 5.3 mmol). After stirring at 90° C. under nitrogen for 2 h, the mixture was cooled to 20° and added potassium carbonate (2.1 g, 15 mmol) and a solution of 3-phenyl-2-propynyl methanesulfonate (945 mg, 4.5 mmol) in dry DMF (2 ml). The reaction was completed after 10 min. stirring. Ice water was added and pH adjusted by addition of 4N HCl (pH 2). The mixture was extracted with ether (3× discarded). The aqueous phase was made basic with ammonia solution (pH 10–11) and the mixture extracted with ether (3×). The extracts were dried (MgSO₄) and the solvent evaporated. The product was taken up in acetone and precipitated with oxalic acid in acetone to give 475 mg (73%) of the title compound. Mp. 154–157° C. (Compound 22).

EXAMPLE 8

The following compounds were made in the same manner as described in example 7 using the appropriate methane sulfonate. The following compounds were isolated as the hydrochloride salt.

1-(3-[3-(4-Chlorophenyl)-2-propyn-1-ylthio]-1,2,5-thiadiazol-4-yl)-4-azatricyclo[2.2.1.0$^{2,6}$]heptane, hydrochloride. Yield: 72%. M.p. 154–156° C. (Compound 23).

1-(3-[3-(3-Chlorophenyl)-2-propyn-1-ylthio]-1,2,5-thiadiazol-4-yl)-4-azatricyclo[2.2.1.0$^{2,6}$]heptane, hydrochloride. Yield: 66%. M.p. 175–177° C. (Compound 24).

1-(3-[3-(3,5-Difluorophenyl)-2-propyn-1-yloxy]-1,2,5-thiadiazol-4-yl)-4-azatricyclo[2.2.1.0$^{2,6}$]heptane, hydrochloride. Yield: 62%. M.p. 173–175° C. (Compound 25).

EXAMPLE 9

4-(4-Azatricyclo[2.2.1.0$^{2,6}$]hept-1-yl)-1,2,5-thiadiazole-3-thiol

A solution of 1-(3-chloro-1,2,5-thiadiazol-4-yl)-4-azatricyclo[2.2.1.0$^{2,6}$]heptane (3.0 g, 14 mmol) and sodium hydrogensulfide, monohydrate (3,14 g, 42 mmol) in dry DMF (80 ml) was stirred at room temperature under nitrogen for 1 h. The solvent was evaporated. Water was added and pH adjusted by addition of 4N HCl (pH 9). The mixture was cooled on ice and the product isolated by filtration to give 1,7 g (58%) of the title compound. M.p. 205–207° C. (Compound 26).

EXAMPLE 10

1-(3-[3-(5-Chloro-2-thienyl)-2-propyn-1-ylthio]-1,2,5-thiadiazol-4-yl)-4-azatricyclo[2.2.1.0$^{2,6}$]heptane, oxalate 4-(4-Azatricycloazatricyclo[2.2.1.0$^{2,6}$]hept-1-yl-1,2,5-thiadiazole-3-thiol (211 mg, 1.0 mmol) in dry THF (10 ml) was added triphenylphosphine (262 mg, 1.0 mmol) and stirred under nitrogen. The mixture was cooled on ice and added 3-(5-chlorothiophen-2-yl)-prop-2-yn-1-ol (259 mg, 1.5 mmol) dissolved in dry THF (5 ml) followed by diethyl azodicarboxylate (174 mg, 1.0 mmol). The mixture was stirred for 16 h starting at 0° C. and allowed to warm to room temperature. Ice water was added and pH adjusted with 4 N HCl to pH 2.0. The reaction mixture was washed with diethylether (2×). The aqueous phase was made basic (pH 10–11) with 25% aqueous ammonia and the product extracted with diethylether (3×). The ether extracts were dried (MgSO₄) and evaporated. Crystallization of the residue with oxalic acid from acetone gave the title compound in 168 mg (37%) yield. M.p. 138–141° C. (Compound 27).

EXAMPLE 11

The following compound was made in the same manner as described in example 10 using the appropriate alcohol. The title compound was purified by flash chromatography before precipitating as a oxalate:

1-(3-[3-(5-Pyrimidyl)-2-propyn-1-ylthio]-1,2,5-thiadiazol-4-yl)-4-azatricyclo[2.2.1.0$^{2,6}$]heptane, oxalate. Yield: 45%. M.p. 174–176° C. (Compound 28).

We claim:

1. A compound of formula I

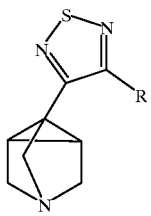

(I)

wherein

R is —OR³ or —SR³ wherein R³ is straight or branched C$_{2-8}$-alkynyl substituted with phenyl which is optionally substituted with one or more selected from halogen(s), —OH, —CF₃, —CN, C$_{1-4}$-alkyl, C$_{1-4}$-alkoxy, C$_{1-4}$-alkylthio, —SCF₃, —OCF₃, —CONH₂ or —CSNH₂; or R is —OR³ or —SR³ wherein R³ is straight or branched C$_{2-8}$-alkynyl substituted with Y wherein Y is a 5 or 6 membered heterocyclic group, which heterocyclic group is optionally substituted at carbon or nitrogen atom(s) with one or more selected from halogen(s), —OH, —CF₃, —CN, C$_{1-4}$-alkyl, C$_{1-4}$-alkoxy, C$_{1-4}$-alkylthio, —SCF₃, —OCF₃, —CONH₂, —CSNH₂, phenyl, benzyl or thienyl, or a carbon atom in the heterocyclic group together with an oxygen atom form a carbonyl group, or which heterocyclic group is optionally fused with a phenyl group; or a pharmaceutically acceptable salt or solvate thereof.

2. A compound according to claim 1 wherein R is —OR³ or SR³, wherein R³ is C$_{2-8}$-alkynyl substituted with phenyl or Y, each of which is optionally substituted with one or more selected from —OH, halogen(s), —CN, C$_{1-4}$-alkyl, C$_{1-4}$-alkylthio, C$_{1-4}$-alkoxy, —SCF₃, —OCF₃, —CF₃, —CONH₂ and —CSNH₂.

3. A compound according to claim 2 wherein R is —OR³ or —SR³, wherein R³ is C$_{2-8}$-alkynyl substituted with phenyl, thiophene, furan, pyrrole, oxazole, thiazole, imidazole, oxadiazole, thiadiazole, pyridine or pyrimidine each of which is optionally substituted with one or more selected from halogen, —CN, C$_{1-4}$-alkoxy or —OCF₃.

4. A compound according to claim 3 wherein R is —OR³ or —SR³, wherein R³ is C$_{2-8}$-alkynyl substituted with phenyl, thiophene, pyridine, pyrimidine or furan, each of which is optionally substituted with one or more selected from halogen, —CN, C$_{1-4}$-alkoxy or —OCF₃.

5. A compound according to claim 2 wherein R is —OR³ or —SR³, wherein R³ is propynyl substituted with phenyl or Y, each of which is optionally substituted with one or more selected from —OH, halogen(s), —CN, C$_{1-4}$-alkyl, C$_{1-4}$-alkylthio, C$_{1-4}$-alkoxy, —SCF₃, —OCF₃, —CF₃, —CONH₂ and —CSNH₂.

6. A compound according to claim 5 wherein R is —OR³ or —SR³, wherein R³ is propynyl substituted with phenyl, thiophene, furan, pyrrole, oxazole, thiazole, imidazole, oxadiazole, thiadiazole, pyridine or pyrimidine, each of which is optionally substituted with one or more selected from halogen, —CN, $C_{1-4}$-alkoxy or —$OCF_3$.

7. A compound according to claim 6 wherein R is —$OR^3$ or —$SR^3$, wherein $R^3$ is propynyl substituted with phenyl, thiophene, pyridine, pyrimidine or furan, each of which is optionally substituted with one or more selected from halogen, —CN, $C_{1-4}$-alkoxy or —$OCF_3$.

8. A compound according to claim 1 which is:

1-(3-[3-(4-fluorophenyl)-2-propynyl-1-oxy]-1,2,5-thiadiazol-4-yl)-4-azatricyclo[2.2.1.0$^{2,6}$]heptane, 1-[3-(3-phenyl-2-propynyl-1-oxy)-1,2,5-thiadiazol-4-yl]-4-azatricyclo[2.2.1.0$^{2,6}$]heptane, 1-[3-(3-phenyl-2-propynylthio)-1,2,5-thiadiazol-4-yl]-4-azatricyclo[2.2.1.0$^{2,6}$]heptane, 1-(3-[3-(3-thienyl)-2-propyn-1-yloxy]-1,2,5-thiadiazol-4-yl)-4-azatricyclo[2.2.1.0$^{2,6}$]heptane, 1-(3-[3-(2-thienyl)-2-propyn-1-yloxy]-1,2,5-thiadiazol-4-yl)-4-azatricyclo[2.2.1.0$^{2,6}$]heptane, 1-(3-[3-(3-methoxyphenyl)-2-propyn-1-yloxy]-1,2,5-thiadiazol-4-yl)-4-azatricyclo[2.2.1.0$^{2,6}$]heptane, 1-(3-[3-(3-pyridyl)-2-propyn-1-yloxy]-1,2,5-thiadiazol-4-yl)-4-azatricyclo[2.2.1.0$^{2,6}$]heptane, 1-(3-[3-(3-furyl)-2-propyn-1-yloxy]-1,2,5-thiadiazol-4-yl)-4-azatricyclo[2.2.1.0$^{2,6}$]heptane, 1-(3-[3-(4-methoxyphenyl)-2-propyn-1-yloxy]-1,2,5-thiadiazol-4-yl)-4-azatricyclo[2.2.1.0$^{2,6}$]heptane, 1-(3-[3-(2-pyridyl)-2-propyn-1-yloxy]-1,2,5-thiadiazol-4-yl)-4-azatricyclo[2.2.1.0$^{2,6}$]heptane, 1-(3-[3-(2-thienyl)-4-methyl-1-pentyn-3-yloxy]-1,2,5-thiadiazol-4-yl)-4-azatricyclo[2.2.1.0$^{2,6}$]heptane, 1-(3-[3-(4-chlorophenyl)-2-propyn-1-yloxy]-1,2,5-thiadiazol-4-yl)-4-azatricyclo[2.2.1.0$^{2,6}$]heptane, 1-(3-[3-(3-chlorophenyl)-2-propyn-1-yloxy]-1,2,5-thiadiazol-4-yl)-4-azatricyclo[2.2.1.0$^{2,6}$]heptane, 1-(3-[3-(3,5-difluorophenyl)-2-propyn-1-yloxy]-1,2,5-thiadiazol-4-yl)-4-azatricyclo[2.2.1.0$^{2,6}$]heptane, 1-(3-[3-(3-trifluoromethylphenyl)-2-propyn-1-yloxy]-1,2,5-thiadiazol-4-yl)-4-azatricyclo[2.2.1.0$^{2,6}$]heptane, 1-(3-[3-(5-chloro-2-thienyl)-2-propyn-1-yloxy]-1,2,5-thiadiazol-4-yl)-4-azatricyclo[2.2.1.0$^{2,6}$]heptane, 1-(3-[3-(3,5-dichlorophenyl)-2-propyn-1-yloxy]-1,2,5-thiadiazol-4-yl)-4-azatricyclo[2.2.1.0$^{2,6}$]heptane, 1-(3-[3-phenyl-2-propynthio]-1,2,5-thiadiazol-4-yl)-4-azatricyclo[2.2.1.0$^{2,6}$]heptane, 1-(3-[3-(4-chlorophenyl)-2-propyn-1-ylthio]-1,2,5-thiadiazol-4-yl)-4-azatricyclo[2.2.1.0$^{2,6}$]heptane, 1-(3-[3-(3-chlorophenyl)-2-propyn-1-ylthio]-1,2,5-thiadiazol-4-yl)-4-azatricyclo[2.2.1.0$^{2,6}$]heptane, 1-(3-[3-(3,5-difluorophenyl)-2-propyn-1-yloxy]-1,2,5-thiadiazol-4-yl)-4-azatricyclo[2.2.1.0$^{2,6}$]heptane, 1-(3-[3-(5-chloro-2-thienyl)-2-propyn-1-ylthio]-1,2,5-thiadiazol-4-yl)-4-azatricyclo[2.2.1.0$^{2,6}$]heptane, 1-(3-[3-(5-pyrimidyl)-2-propyn-1-ylthio]-1,2,5-thiadiazol-4-yl)-4-azatricyclo[2.2.1.0$^{2,6}$]heptane, 1-(3-[3-(3-trifluoromethoxyphenyl)-2-propyn-1-yloxy]-1,2,5-thiadiazol-4-yl)-4-azatricyclo[2.2.1.0$^{2,6}$]heptane, or a pharmaceutically acceptable salt or solvate thereof.

9. A pharmaceutical composition comprising a compound according to claim 1 together with one or more pharmaceutically acceptable carriers or diluents.

10. The pharmaceutical composition according to claim 9 in the form of an oral dosage unit or parenteral dosage unit.

11. The pharmaceutical composition according to claim 10, wherein said dosage unit comprises from about 0.1 to about 100 mg of the compound.

12. A method of treating a disease in the central nervous system caused by malfunctioning of the muscarinic cholinergic system comprising administering to a subject in need thereof an effective amount of a compound according to claim 1.

13. A method of treating a disease in the central nervous system caused by malfunctioning of the muscarinic cholinergic system comprising administering to a subject in need thereof a pharmaceutical composition according to claim 9.

14. A method for treating a condition associated with the modulation of a muscarinic cholinergic receptor comprising administering to a subject in need thereof an effective amount of a compound according to claim 1.

15. A method for interacting with a muscarinic cholinergic receptor comprising administering to a subject in need thereof an effective amount of a compound according to claim 1.

* * * * *